United States Patent
Chey et al.

(10) Patent No.: US 8,723,534 B2
(45) Date of Patent: May 13, 2014

(54) METHODS AND APPARATUS FOR DETECTION OF GASEOUS CORROSIVE CONTAMINANTS

(75) Inventors: S. Jay Chey, Hartsdale, NY (US);
Hendrik F. Hamann, Yorktown Heights, NY (US); Levente I. Klein, Tuckahoe, NY (US); Michael A. Schappert, Wappingers Falls, NY (US); Prabjit Singh, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 540 days.

(21) Appl. No.: 12/987,353

(22) Filed: Jan. 10, 2011

(65) Prior Publication Data
US 2012/0176148 A1    Jul. 12, 2012

(51) Int. Cl.
*H01L 21/00* (2006.01)
*G01N 27/403* (2006.01)
*G01N 17/04* (2006.01)
*G01N 17/00* (2006.01)

(52) U.S. Cl.
CPC .... *G01N 17/046* (2013.01); *H05K 2201/09736* (2013.01); *G01N 17/00* (2013.01)
USPC .............................. 324/700; 438/49; 257/253

(58) Field of Classification Search
CPC ................ G01N 17/046; G01N 17/00; H05K 2201/09736
USPC ................ 324/700; 438/49; 257/253; 347/65
See application file for complete search history.

(56) References Cited

U.S. PATENT DOCUMENTS

| | | | |
|---|---|---|---|
| 4,869,874 | A | 9/1989 | Falat |
| 5,139,627 | A | 8/1992 | Eden et al. |
| 5,411,890 | A | 5/1995 | Falat |
| 5,446,369 | A | 8/1995 | Byrne et al. |
| 6,015,484 | A | 1/2000 | Martinchek et al. |
| 6,564,620 | B1 | 5/2003 | Jaeger |
| 7,185,531 | B2 | 3/2007 | Souers |
| 7,388,386 | B2 | 6/2008 | Ramgopal et al. |
| 2004/0149594 | A1 | 8/2004 | Eden |
| 2006/0125493 | A1 | 6/2006 | Subramanian et al. |
| 2007/0199379 | A1 | 8/2007 | Wolf et al. |
| 2010/0072884 | A1* | 3/2010 | Tchakarov et al. ........... 313/504 |
| 2010/0192688 | A1* | 8/2010 | Humbert et al. ........... 73/335.03 |

OTHER PUBLICATIONS

Murcko, R.M., "Corrosion-Indicating Device" IBM Technical Disclosure Bulletin (Mar. 1, 1990) pp. 25, vol. 32(10A).
Long, T.C. et al., "Thin Film Corrosion-Indicating Bridge" IBM Technical Disclosure Bulletin (Apr. 1, 1989) pp. 285-287.

(Continued)

*Primary Examiner* — Jermele M Hollington
*Assistant Examiner* — Farhana Hoque
(74) *Attorney, Agent, or Firm* — Scully, Scott, Murphy & Presser, P.C.; Vazken Alexanian

(57) ABSTRACT

A corrosion sensor includes a plurality of metal strips having different thicknesses. A first metal strip with the least thickness is first employed to provide sensitive corrosion detection. After an exposed portion of the first metal strip is consumed, a second metal strip having a second least thickness can be employed to provide continued sensitive corrosion detection employing a remaining un-corroded portion of the second metal strip. The plurality of metal strips can be sequentially employed as exposed portions of thinner metal strips become unusable through complete corrosion and un-corroded exposed portions of thicker metal strips become thin enough to provide sensitive corrosion detection.

18 Claims, 6 Drawing Sheets

(56) References Cited

OTHER PUBLICATIONS

Minamitani, R. et al., "Corrosion Sensors to Evaluate Corrosiveness of Installation Environment for Electronic Equipment" Corrosion Engineering—Tokyo—(2005) pp. 476-482, vol. 54, Part 10 (English-language abstract only).

Liptak, B.G., Instrument Engineers' Handbook, (vol. 1) Fourth Edition: Process Measurement and Analysis, CRC Press (2003) pp. 1332-1333.

* cited by examiner

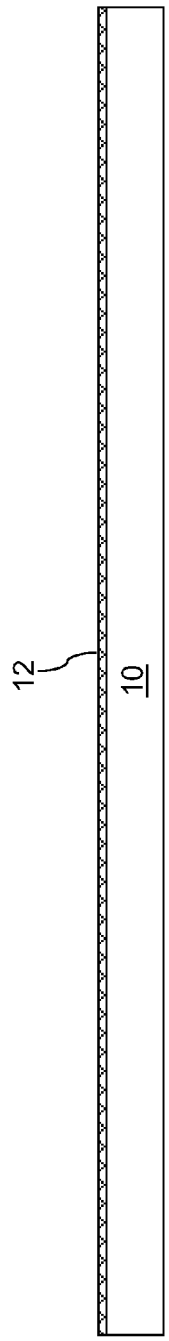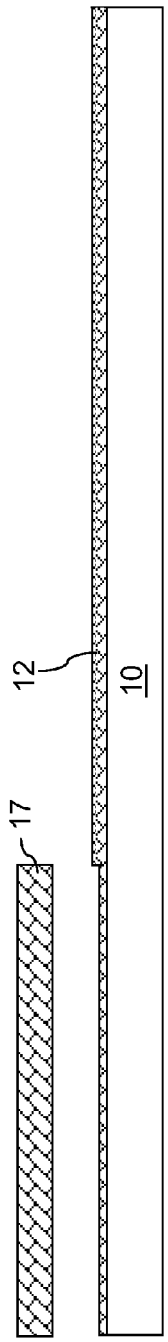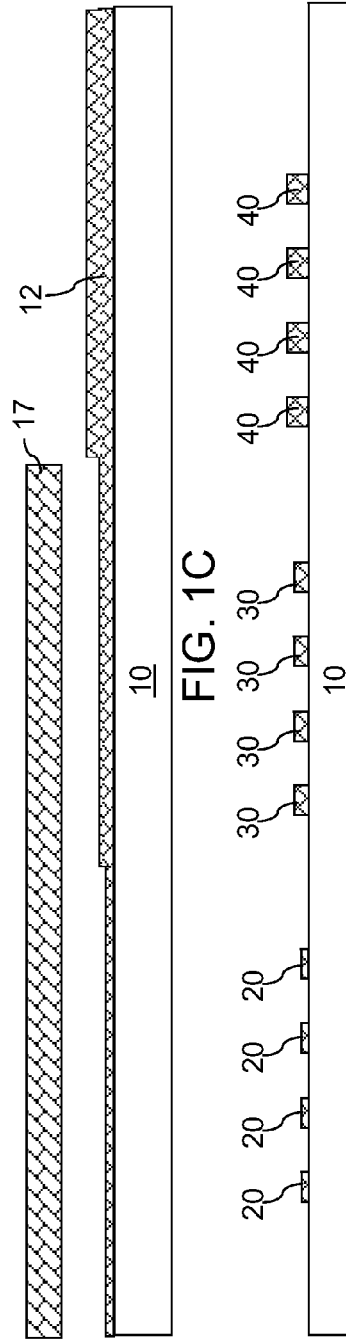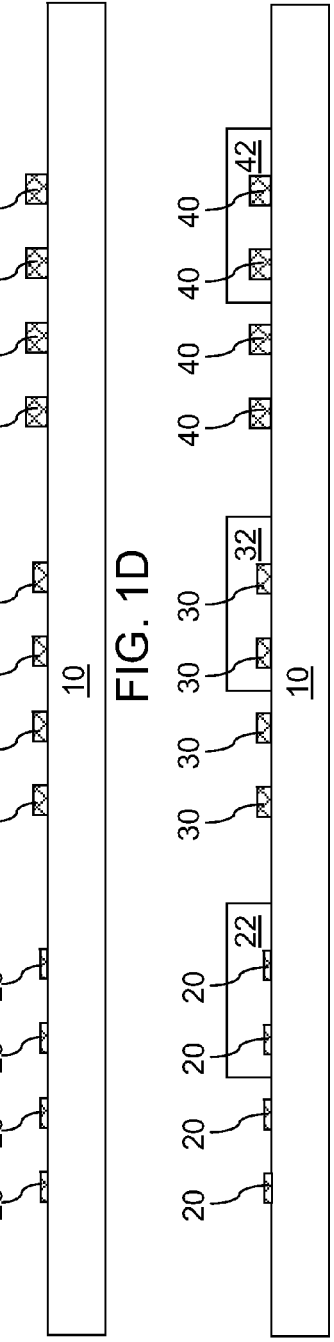

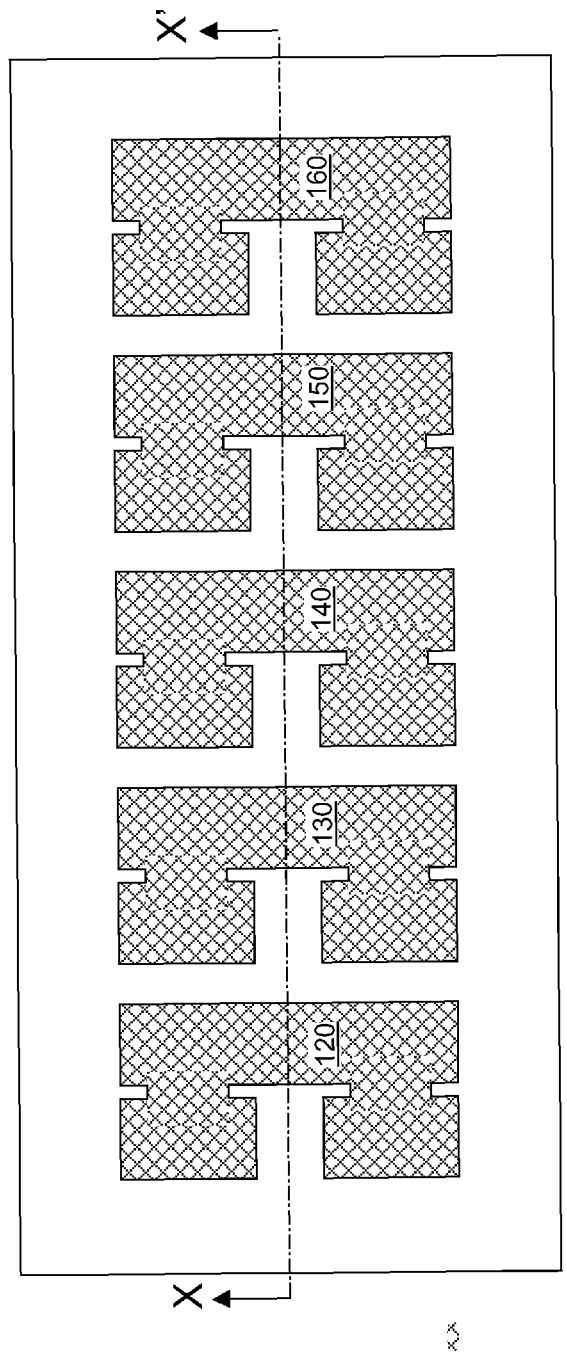
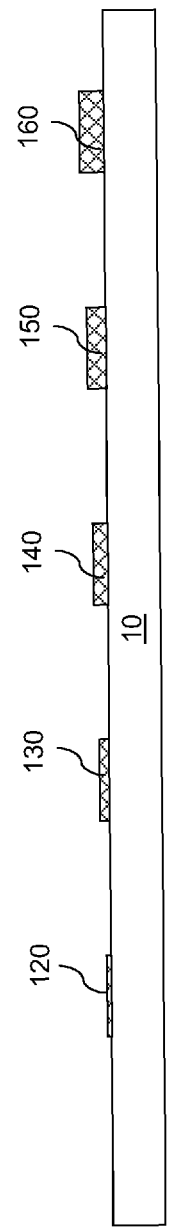
FIG. 5A
FIG. 5B

METHODS AND APPARATUS FOR DETECTION OF GASEOUS CORROSIVE CONTAMINANTS

BACKGROUND

The present disclosure relates to methods of detecting gaseous contaminants that cause corrosion and apparatuses for effecting the same.

Corrosion is a common issue in aeronautic industry, clean rooms, paper industry, waste water treatment plant, and many other industrial facilities. In an illustrative example, data centers employing mission critical Information Technology infrastructures and computers are geographically spanning around the world to provide faster access to users. Some of such data centers are located in geographical areas rich in sulphurous gaseous contaminations. Many hardware failures associated with silver and copper corrosion of thin film resistors, power switches and/or circuit boards components at such geographical areas are well known. Detection of gaseous corrosive contaminants is, therefore, necessary to anticipate, and to take preventive steps for, corrosion of computer hardware at areas susceptible to corrosion through gaseous corrosive contaminants.

Current commonly used corrosion detection techniques rely on weight measurement of silver and copper coupons due to simplicity and ease. Corrosion detection technique known in the art is not sensitive enough to detect corrosion rates under 10 nm per month, and requires an extensive exposure time in a corrosive environment. The result provided by coupon measurements provides a weighted corrosion rate over an extended period of time without specifically pointing to temporal variation of the corrosion in the data centers.

In order to provide improved corrosion sensitivity, the corrosion product has to produce a sizeable change in the detection signal. In case of resistive technique, where change in resistance due to thickness film variation is measured as the film is exposed to the corrosive environment, the thickness of a metallic film needs to be sufficiently small such that the thickness of a corroded portion of a metallic film is significant relative to a total film thickness. However, the thickness of the metallic film in prior art corrosion detectors is constrained by the lifetime of the corrosion detectors. Specifically, corrosion detectors are designed to be operational over a significant period of time without requiring replacement. In practical terms, replacing corrosion sensors every month or two in order to obtain high sensitivity is an expensive and time consuming proposition, and is not a practicable solution.

Additional requirements for effective corrosion sensors relates to separation of the corrosion effect from fluctuation of temperature and humidity and mechanically robustness so that the performance of the corrosion sensors is not affected by disturbances caused by strong air streams commonly encountered in data center environments. Furthermore, there is demand for real time corrosion detectors that can assess both the indoor and outdoor environment.

BRIEF SUMMARY

A corrosion sensor including a plurality of metal strips having different thicknesses is provided. A first metal strip with the least thickness is first employed to provide sensitive corrosion detection. After an exposed portion of the first metal strip is consumed, a second metal strip having a second least thickness can be employed to provide continued sensitive corrosion detection employing a remaining un-corroded portion of the second metal strip. The plurality of metal strips can be sequentially employed as exposed portions of thinner metal strips become unusable through complete corrosion and un-corroded exposed portions of thicker metal strips become thin enough to provide sensitive corrosion detection. In one embodiment, each metal strip has a constant width and includes an exposed strip portion and a protected strip portion that are connected to each other in a series connection, and electrical current passes through the serial connection. Voltage differences across the exposed strip portion and the protected strip portion are compared to determine the fractional change in the film thickness in the exposed strip portion. In another embodiment, the plurality of metal strips can be provided for direct measurement of resistance without employing a reference resistor. In this embodiment, the corrosion rate of the metal in the plurality of metal strips can be calculated based on discrete resistance measurements on the plurality of metal strips.

According to an aspect of the present disclosure, a corrosion detection apparatus includes a plurality of metal strips located on an insulating surface of a substrate and having different thicknesses. A first contact pad is attached to one end of each metal strip among the plurality of metal strips, and a second contact pad is attached to another end of each metal strip among the plurality of metal strips.

According to another aspect of the present disclosure, a method of detecting corrosion-accelerating gases includes providing a corrosion detection apparatus comprising a plurality of metal strips located on an insulating surface of a substrate and having different thicknesses; determining a first corrosion rate for a first time period at a location based on measured data on a resistance change in a first metal strip among the plurality of metal strips; and determining a second corrosion rate for a second time period at the location based on measured data on a resistance change in a second metal strip among the plurality of metal strips. The second metal strip is thicker than the first metal strip, and the second time period includes at least a time period subsequent to the first time period. The first time period may extend to a time at which corrosion causes the first metal strip to become electrically open. All, or a plurality, of the metal strips in the corrosion detection apparatus can measure the corrosion simultaneously. For example, a measurement scheme may employ the first metal strip throughout a first lifetime, which is the lifetime of the first metal strip until the first metal strip becomes electrically open, and subsequently employ the second metal strip until the second metal strip becomes electrically open, and then sequentially employ an i-th metal strip until the i-th metal strip becomes electrically open until all metal strips become electrically open, in which each i-th metal strip is thicker than (i−1)-th strip for each i greater than 2. Optionally, the second metal strip may be employed concurrently with the use of the first metal strip.

BRIEF DESCRIPTION OF THE SEVERAL VIEWS OF THE DRAWINGS

FIGS. 1A-1E are sequential vertical cross-sectional views of a first exemplary apparatus for detection of corrosion-accelerating gases at various stages of a manufacturing process according to a first embodiment of the present disclosure.

FIG. 5A is a top-down view of a second exemplary apparatus for detection of corrosion-accelerating gases according to a second embodiment of the present disclosure.

FIG. 5B is a vertical cross-sectional view of the second exemplary apparatus along the plane X-X' in FIG. 4A according to the second embodiment of the present disclosure.

DETAILED DESCRIPTION

Figure 2:
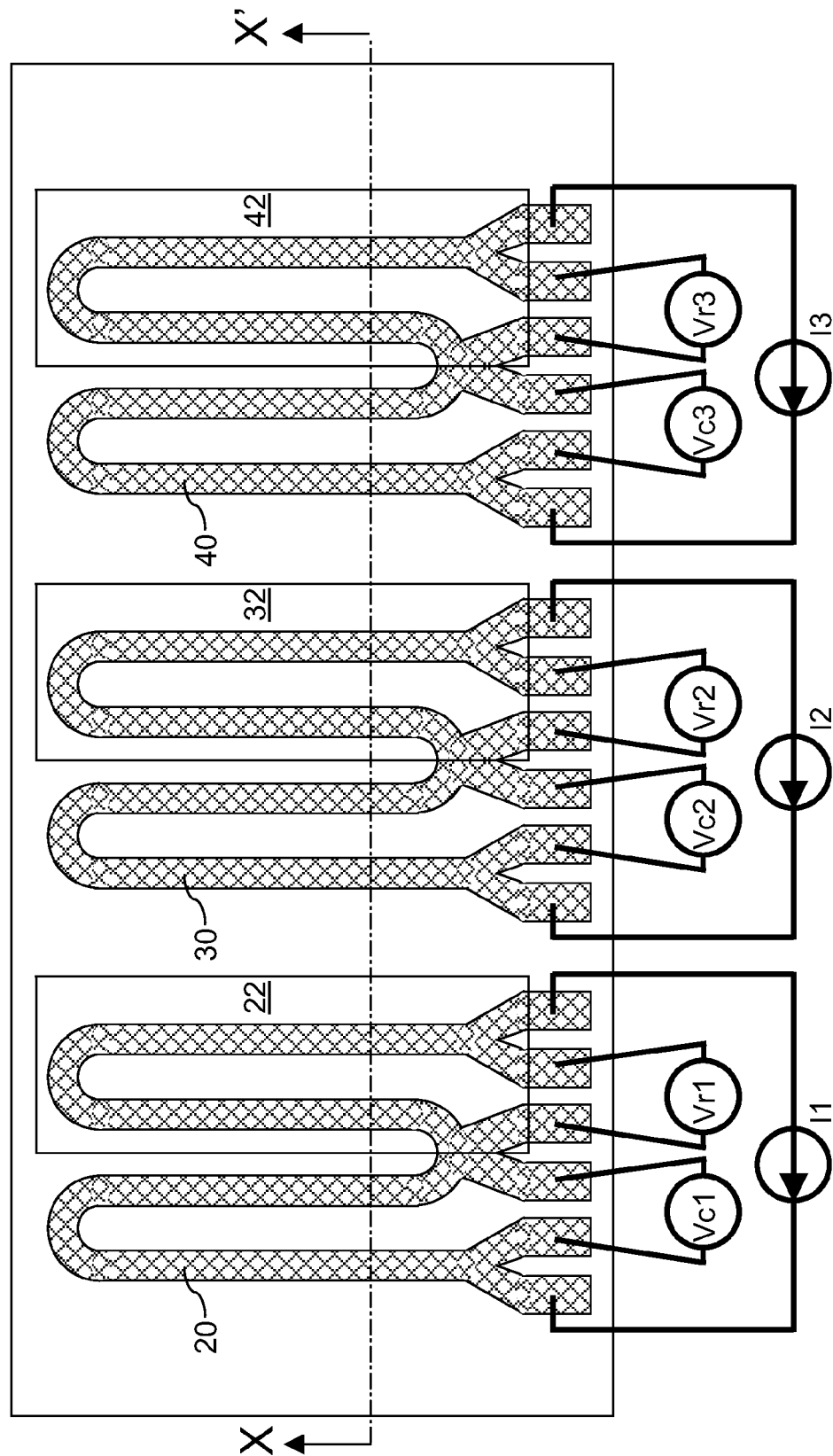
FIG. 2 is a top view of the first exemplary apparatus in FIG. 1E according to the first embodiment of the present disclosure. The vertical plane X-X' corresponds to the plane of the vertical cross-sectional view of FIG. 1E.

As stated above, the present disclosure relates to methods of detecting atmospheric contamination in mission critical facilities by measuring the reactivity of thin metal films due to exposure to gaseous contaminants and apparatuses for effecting the same, which are now described in detail with accompanying figures. Throughout the drawings, the same reference numerals or letters are used to designate like or equivalent elements. The drawings are not necessarily drawn to scale.

A corrosion sensor apparatus that has sensitivity of 1 angstrom per day or better and an operational lifetime of at least a year is provided in the present disclosure. The corrosion sensor is based on resistive detection of thickness reduction of a plurality of metal strips, each of which is a thin metal film exposed to a corrosive environment. The length and width of each metal strip in the corrosion sensor apparatus are much greater than the thickness thereof such that the effect of variation of the length and width on the resistance of each metal strip is less than 0.1% of the total resistance change. As the corrosion proceeds, each metal strip is electrochemically transforming into a nonconductive film covering the top surface of the thin metal film. The corrosion proceeds as the reactive gas diffuses through the nonconductive barrier and gradually consumes the underlying conductive portion of the metal films. The reduced thickness results in an increase in the resistance of the thin film. The change in the resistance of the corroded thin film can be detected by electrical measurements.

In general, in order to detect small corrosion rates, the corrosion product has to produce a sizable change in the detection signal. For resistive measurement, the change in resistance of a metal film due to corrosion has to be within 1 ppm to be detected by electrical measurements. The metal film must be thin enough to cause a detectable change in the resistance. Because a metal film as a corrosion sensor is no longer usable once all of the metal film is corroded, a metal film with a small thickness also has a short lifetime.

In order to overcome this difficulty, multiple metal films having different film thicknesses are fabricated on the same substrate. The film thickness can vary in well defined ratios such that a first film having the least thickness and being the most sensitive unit, i.e., the thinnest film sensor, can be used for a first period of time. When the first film is consumed by corrosion, a second film having the second least thickness is utilized for a second period of time that follows the first period of time until the second film corroded. When the second film is consumed by corrosion, a third film having the third least thickness is utilized for a third period of time that follows the second period of time until the third film is corroded, and so on until the thickest film is consumed by corrosion. Thus, a corrosion detection apparatus is provided, which includes a plurality of corrosion sensors employing metal films having different thicknesses and configured to be sequentially employed during different periods of time. The corrosion detection apparatus can include corrosion sensors with sensitivity of 0.1 nm per day in corrosion rate and a large signal to noise ratio. The corrosion detection apparatus can be employed for gaseous contamination monitoring at any facility requiring monitoring of such gaseous contamination in the ambient.

FIGS. 1A-1E illustrate a manufacturing process for a first exemplary apparatus that can be employed for detection of corrosion-accelerating gases in sequential vertical cross-sectional views according to a first embodiment of the present disclosure. Referring to FIG. 1A, a metal film 12 is deposited on an insulating surface of a substrate 10. The substrate 10 can be an insulating substrate such as a glass substrate, a sapphire ($Al_2O_3$) substrate, or a plastic substrate, or can be any substrate having an insulating top layer. The thickness of the substrate 10 is selected to provide sufficient mechanical strength to the first exemplary apparatus for handling purposes. For example, the thickness of the substrate 10 can be from 50 microns to 1 cm, although lesser and greater thicknesses can also be employed.

The metal film 12 includes a metal that is susceptible to corrosion by corrosion-accelerating gases. Corrosion-accelerating gases refer to any gas that can facilitate or accelerate formation of a corroded metal compound by directly interacting with, either alone or in combination with at least another gas, at least one transition metal. Corrosion-accelerating gases include, but are not limited to, $H_2S$, $SO_2$, $NO$, $NO_2$, $N_2O_3$, $Cl_2$, and $O_3$. The metal in the metal film 12 can be selected such that the metal is susceptible to corrosion by at least one of $H_2S$, $SO_2$, $NO$, $NO_2$, $N_2O_3$, $Cl_2$, and $O_3$. For example, the metal in the metal film 12 can be selected from silver, copper, brass, zinc, aluminum and iron. The metal can be deposited, for example, by vacuum evaporation or physical vapor deposition (sputtering).

The thickness of the metal film 12 at this point is selected to enable detection of corrosion-accelerating gases with high sensitivity without regard to the lifetime of a metal film as a sensor. Thus, any thickness that enables formation of a continuous metal film with uniformity in the thickness can be selected. For example, the thickness of the metal film 12 can be in a range from 3 nm to 250 nm, and typically from 25 nm to 100 nm, although lesser and greater thicknesses can also be employed. The thickness of the metal film 12 at the end of the processing step of FIG. 1A is herein referred to as a "first thickness."

Referring to FIG. 1B, a stencil mask 17 is employed to block deposition of additional metal in a first area of the metal film 12, which is the area shielded by the stencil mask 17, while allowing deposition of additional metal in the rest of the area of the metal film 12. The thickness of the metal film 12 in the first area remains constant, while the thickness in the rest of the area of the metal film 12 increases to a greater thickness by the end of the processing step of FIG. 1B, which is herein referred to as a "second thickness." In a non-limiting illustrative example, the stencil mask 17 can be a perforated metal mask that is placed over the substrate 10. The metal film 12 can be deposited through the stencil mask 17. Multiple different depositions can be performed with a movement of the stencil mask 17 between depositions or any other type of mechanical re-arrangement of the relative alignment of the openings in the stencil mask 17 to form metal films 12 having different thicknesses. Any other mechanical arrangement can be employed in combination with multiple depositions to form metal films 12 having different thicknesses.

In one embodiment, the difference between the second thickness and the first thickness can be in a range from 3 nm to 250 nm, and typically from 25 nm to 100 nm, although lesser and greater thicknesses can also be employed. The first thickness and the second thickness can be integer multiples of a common denominator thickness such that the first thickness is a first integer times the common denominator thickness and the second thickness is a second integer times the common denominator thickness, and the first integer and the second integer do not exceed 10. Preferably, the first integer and the second integer do not exceed 5. In one case, the first integer can be 1 and the second integer can be 2, i.e., the second thickness can be twice the first thickness.

Referring to FIG. 1C, the stencil mask 17 and/or at least another stencil mask (not shown) can be employed to block deposition of additional metal in at least one area including the first area of the metal film 12, while allowing deposition of additional metal in the rest of the area of the metal film 12 in one or more deposition steps. The thickness of the metal film 12 in the blocked area remains constant, while the thickness in the rest of the area of the metal film 12 increases to a greater thickness in each deposition step. Each additional deposition step forms areas having a greater thickness so that a third area having a third thickness that is greater than the second thickness can be formed, and so on until an n-th area having an n-th thickness that is greater than the (n−1)-th thickness can be formed. For each integer i between 1 and (n+1), an i-th area has an i-th thickness that is greater than (i−1)-th thickness within the metal film 12.

In one embodiment, the difference between the i-th thickness and the (i−1)-th thickness can be in a range from 3 nm to 250 nm, and typically from 25 nm to 100 nm for each integer i between 1 and (n+1), although lesser and greater thicknesses can also be employed. The (i−1)-th thickness and the i-th thickness can be integer multiples of a common denominator thickness such that the (i−1)-th thickness is an (i−1)-th integer times the common denominator thickness and the i-th thickness is an i-th integer times the common denominator thickness for each integer i between 1 and (n+1). In some cases, a set of integers can be selected such that the (i−1)-th integer and the i-th integer do not exceed 10 times n, i.e., the total number of different thicknesses, for each integer i between 1 and (n+1). In one case, the common denominator thickness can be the first thickness so that all thicknesses among the n different thicknesses are integer multiples of the first thickness. In this case, the different thicknesses in the metal film 12 can be integer multiples of a minimum thickness among the different thicknesses, i.e., the integer multiples of the first thickness.

While FIGS. 1A-1C illustrate a scheme in which a stencil mask 17 gradually covers more areas, different schemes that alter the sequence of blocking can also be employed. For example, the stencil mask 17 may be employed to gradually expose more areas of the metal film 12 for deposition in each successive deposition steps. In general, the sequence of blocking can be altered in any manner provided that multiple areas having different thicknesses are formed within the metal film 12. The metal film 12 includes a plurality of portions having different thicknesses, and is located on an insulating surface of the substrate 10.

Referring to FIG. 1D, the metal film 12 can be patterned, for example, by a combination of lithographic techniques that forms a patterned photoresist (not shown) on the metal film 12 and an etch that employs the patterned photoresist as an etch mask. A plurality of metal strips having different thicknesses are formed on the insulting surface of the substrate 10. The plurality of metal strips can include a first metal strip 20 having the first thickness, i.e., which is the thinnest metal strip, and i-th metal strips having the i-th thickness for each integer i between 1 and (n+1), i.e., for each integer including 2 and n and all integers between 2 and n. Thus, the plurality of metal strips can include a second metal strip 30 having the second thickness and an n-th metal strip 40 having the n-th thickness and any additional i-th metal strip (not shown) having the i-th thickness in which i is any integer greater than 2 and less than n. Each of the plurality of metal strips (20, 30, 40) is formed on the insulating surface of the substrate 10.

The relationships among thicknesses of the different areas of the metal film 12 in FIG. 1C are transferred without changes to the relationship among thickness of the plurality of metal films (20, 30, 40). Each i-th metal strip has the i-th thickness for each positive integer i less than (n+1). Thus, the differences in thicknesses of the plurality of metal strips (20, 30, 40) can be integer multiples of a difference between a pair of metal strips among the plurality of metal strips (20, 30, 40). The different thicknesses in the plurality of metal strips (20, 30, 40) can be in a range from 3 nm to 1,000 nm, and typically from 25 nm to 500 nm, although lesser and greater thicknesses can also be employed. The difference between a pair of metal strips including an i-th metal strip and an (i−1)-th metal strip can be in a range from 3 nm to 250 nm, and typically from 25 nm to 500 nm, for each i greater than 1 and less than (n+1), although lesser and greater thickness differentials can also be employed.

Referring to FIGS. 1E and 2, a corrosion detection apparatus according to the first embodiment of the present disclosure can be formed by depositing a dielectric material over the plurality of metal strips (20, 30, 40) and the substrate 10 and subsequently patterning the dielectric material. The patterning of the electric material can be performed, for example, by a combination of lithographic techniques that forms a patterned photoresist (not shown) over the dielectric material and an etch that employs the patterned photoresist as an etch mask. The pattern in the photoresist is selected so that a portion of each of the plurality of metal strips (20, 30, 40) is exposed, while another portion of each of the plurality of metal strips (20, 30, 40) is covered by a dielectric material portion. Each metal strip among the plurality of metal strips (20, 30, 40) includes an exposed strip portion and a protected strip portion that are connected to each other in a series connection.

The dielectric material portions cover the protected strip portions, and do not cover the exposed strip portions. The dielectric material portions can include a first dielectric material portion 22 that overlies a protected strip portion within the first metal strip 20 and i-th dielectric material portions metal overlying a protected strip portion of the i-th metal strip for each integer i between 1 and (n+1). Thus, the dielectric material portions can include a second dielectric material portion 32 overlying and hermatically sealing a protected strip portion within the second metal strip 30 and an n-th dielectric material portion 42 overlying and hermatically sealing a protected strip portion within the n-th metal strip 40 and any additional i-th dielectric material portion (not shown) overlying and hermatically sealing a protected strip portion within the i-th metal strip (not shown) in which i is any integer greater than 2 and less than n.

While the first dielectric metal portion 22, the second dielectric metal portion 32, and the n-th dielectric metal portion 42 are illustrated as rectangular shapes in FIG. 2 through which the protected strip portions of the first metal strip 20, the second metal strip 30, and the n-th metal strip 40 are visible, respectively, the first dielectric metal portion 22, the second dielectric metal portion 32, and the n-th dielectric metal portion 42 may, or may not, be optically transparent. The dielectric material can be selected from materials that are not permeable to corrosion-accelerating gases. Exemplary dielectric materials that are not permeable to corrosion-accelerating gases include polystyrene polymer, silicon nitride, aluminum oxide, and other dielectric metal oxides and dielectric metal oxynitrides.

The first exemplary structure of FIGS. 1E and 2 functions as a corrosion detection apparatus. The corrosion detection apparatus includes the plurality of metal strips (20, 30, 40) located on an insulating surface of the substrate 10 and having different thicknesses. The patterning of the metal film 12 at the processing step of FIG. 1D is performed such that a first contact pad is attached to one end of each metal strip among the plurality of metal strips (20, 30, 40) and a second contact pad is attached to another end of each metal strip among the plurality of metal strips (20, 30, 40) after the patterning. Each metal strip among the plurality of metal strips (20, 30, 40) includes an exposed strip portion and a protected strip portion that are connected to each other in a series connection. As discussed above, the different thicknesses can be integer multiples of a minimum thickness among the different thicknesses. Further, differences in thicknesses of the plurality of metal strips can be integer multiples of a difference between a pair of metal strips among the plurality of metal strips.

Each metal strip among the plurality of metal strips (20, 30, 40) can have a constant width. For example, the width of each metal strip can be set such the width is at least one order of magnitude, and preferably at least two orders of magnitude, greater than the thickness of the metal strip in order to minimize the contribution of the lateral corrosion to measured resistance change. Each metal strip forms a single corrosion sensor including two arms. One arm includes a protected metal portion which is covered and protected by a dielectric material portion (22, 32, or 42). Thus, the protected metal portion is not corroded in any significant way during the operation of the corrosion sensor. The other arm includes an exposed metal portion which is exposed to the ambient gases of the environment. Contact pads are attached to both arms so as to enable four point probe measurements which provide accurate measurements of resistance shift in the arm that includes the exposed metal portion. Contact pads can be made wider than the widths of metal strips in order to minimize the contribution of the contact resistance especially for thinner metal strips, e.g., the first metal strip 20.

In one embodiment, the exposed strip portion and the protected strip portion can have a same resistance within each metal strip. Optionally, the exposed strip portion and the protected strip portion can have the same thickness, the same width, the same length, and the same shape in addition to the same material except for the difference of the presence or absence of a dielectric material portion thereabove.

In another embodiment, the exposed strip portion and the protected strip portion can have a constant width within each metal strip such that the width is greater than ten times the thickness of the metal strip which includes the exposed strip portion and the protected strip portion.

In yet another embodiment, the exposed strip portion and the protected strip portion can have the same length within each metal strip such that the length is greater than one hundred times the thickness of the metal strip that includes the exposed strip portion and the protected strip portion.

Four point electrical measurements can be performed, for example, by providing a current source that provides constant electrical current through the exposed strip portion and the protected strip portion within a given metal strip, a first voltmeter configured to measure a voltage difference across the exposed strip portion in the metal strip, and a second voltmeter configured to measure a voltage difference across the protected strip portion in the metal strip. For example, current sources are labeled I1, I2, and I3, first voltmeters are labeled Vc1, Vc2, and Vc3, and second voltmeters are labeled Vr1, Vr2, and Vr3 in FIG. 2.

The currents I1, I2, and I3 are optimized such that it will maintain the same sensitivity to corrosion once the detection is switched from one sensor to the other. The reference resistor value will decrease as the film thickness is increased but the current value will compensate for this change.

During the operation of the corrosion detection apparatus of FIGS. 1E and 2, the exposed strip portions are corroded due to exposure to corrosion-accelerating gases from the outer surface and inward toward the surface of the substrate 10. The resistance of an exposed strip portion changes, i.e., increases, as the thickness of a non-corroded portion decreases with the corresponding increase of the thickness of a corroded portion within each exposed strip portion. The corroded portions of the metal strips can include a metal oxide, a metal chloride, and/or a metal sulfide that are not electrically conductive. If a metal strip includes silver or copper prior to corrosion, the corroded portions of the metal strip can include, for example, $Ag_2S$, $Ag_2O$, $AgCl$, $Cu_2O$, and/or $Cu_2S$, which are not electrically conductive.

The corrosion rate of an ambient at a particular location can be determined by placing the corrosion detection apparatus at that location and performing periodic electric measurements. At periodic intervals, e.g., every minute, every hour, every day, every week, or every month, electrical current can be applied through the series connection of the exposed strip portion and the protected strip portion within a metal strip. A first voltage difference across the exposed strip portion and a second voltage difference across the protected strip portion are measured while the electrical current is flowing. A corrosion rate can be determined based on the ratio of the second voltage difference to the first voltage difference and the thickness of the protected strip portion within the metal strip, which is the same as the original thickness of the exposed strip portion within the metal strip.

The corrosion detection apparatus is a composite corrosion sensor including a plurality of metal strips, each of which functions as a single corrosion sensor. Each corrosion sensor employs a metal strip having film thickness from other metal strips and including a resistor element that is susceptible to corrosion. Each corrosion sensor employing a single metal strip is functionally interchangeable with another corrosion sensor if both corrosion sensors are operational. As the thickness of an uncorroded portion in an exposed strip portion decreases due to corrosion, the resistance of the exposed strip portion increases correspondingly. The increase in the resistance of the exposed strip portion can be compared with a reference resistance, which is the resistance of the protected strip portion located within the same metal strip, shielded from the corrosive environment, and maintains the same resistance throughout the operation of the corrosion detector apparatus.

A non-limiting illustrative example of a corrosion sensor device employing a current sensor with enhanced sensitivity is provided herein. An exemplary exposed strip portion of a metal strip can have a thickness of 30 nm and have a resistance of 50 Ohms. A 0.1 nm reduction in the film thickness result in an changed resistance of:

$$R = R_0 \frac{30 \text{ nm}}{29.9 \text{ nm}} = 50.167 \text{ }\Omega.$$

Assuming that electrical current of 1 mA flows through the exposed strip portion of the metal strip, 0.167 mV change is detected at the first voltmeter that measures the voltage across the exposed strip portion. If a voltage amplification stage providing a gain of 100 is connected to the first voltmeter, the output of the voltage amplification stage can provide a voltage variation of 16.7 mV. Such a change in voltage at the voltage amplification stage can be easily detected by employing standard electronics circuitry.

Another benefit provided by such a voltage detection scheme is signal immunity to temperature variations. Although that the resistivity of a metal film changes with temperature fluctuations at the location of measurement, a differential resistance measurement can be employed in which the resistance of the exposed strip portion is compared with the resistance of the protected strip portion at the time of the measurement. The corrosion thickness, i.e., the decrease in the conducting portion of the exposed strip portion, can be calculated assuming that the resistivity changes with the same temperature dependence both for a reference resistor, which is the protected strip portion, and a corroding resistor, which is the exposed strip portion. In this case the corrosion thickness $\Delta t_{corr}$ can be approximated by:

$$\Delta t_{corr} = t\left(1 - \frac{V_{ref}}{V_{corr}} \frac{R_{corr}^0}{R_{ref}^0}\right),$$

in which t is the initial thickness of the exposed metal film, which is the same as the thickness of the reference thin film resistor at any time, $V_{ref}$ is the measured voltage across the reference resistor, $V_{corr}$ is the measured voltage across the corroding resistor, $R_{ref}^0$ is the initial resistance of the reference resistor, and $R_{corr}^0$ is the initial resistance of the corroding resistor. Thus, the error introduced by temperature variations can be minimized by concurrent measurement of resistance variation of reference and corroding metal films.

In general, a sensitive corrosion detector apparatus can be constructed by including a series of corrosion sensors, each including a pair of a corroding resistor, i.e., an exposed strip portion, and a reference resistor, i.e., a protected strip portion. The ratio of thicknesses can be selected to be expressible with integers having a magnitude on the order of the total number n of the metal strips, i.e., integers having a magnitude that does not exceed ten times the total number n of the metal strips.

One simple implementation of the corrosion detector apparatus includes a sequence of corrosion sensors including metal strips (including exposed and protected strip portions) that have thickness integer multiples of the minimum thickness, e.g., 30 nm, 60 nm, 90 nm, 120 nm, 150 nm, and 180 nm. All corroding resistors in the corrosion detector apparatus are exposed to the corrosive environment at the same time. If the corrosion rate at a location is maintained at a constant rate of 30 nm per month, the first corrosion sensor including a corroding resistor with an initial thickness of 30 nm is employed during the first month to provide data on the corrosion rate, and is consumed by the end of the first month of operation. Once the first corrosion sensor is consumed, a second corrosion sensor, which has a remaining uncorroded thickness of 30 nm in the corroding resistor at the beginning of the second month, can be employed during the second month to provide data on the corrosion rate, and is consumed by the end of the second month of operation. For every integer value of i greater than 1 and less than (n+1), Once the (i−1)-th corrosion sensor is consumed, an i-th corrosion sensor, which has a remaining uncorroded thickness of 30 nm in the corroding resistor at the beginning of the i-th month, can be employed during the i-th month to provide data on the corrosion rate, and is consumed by the end of the i-th month of operation. The sequential use of the corrosion sensors can preserve the sensitivity of the first corrosion sensor having the least thickness, while providing an extended lifetime for the corrosion detection apparatus.

Figure 3:
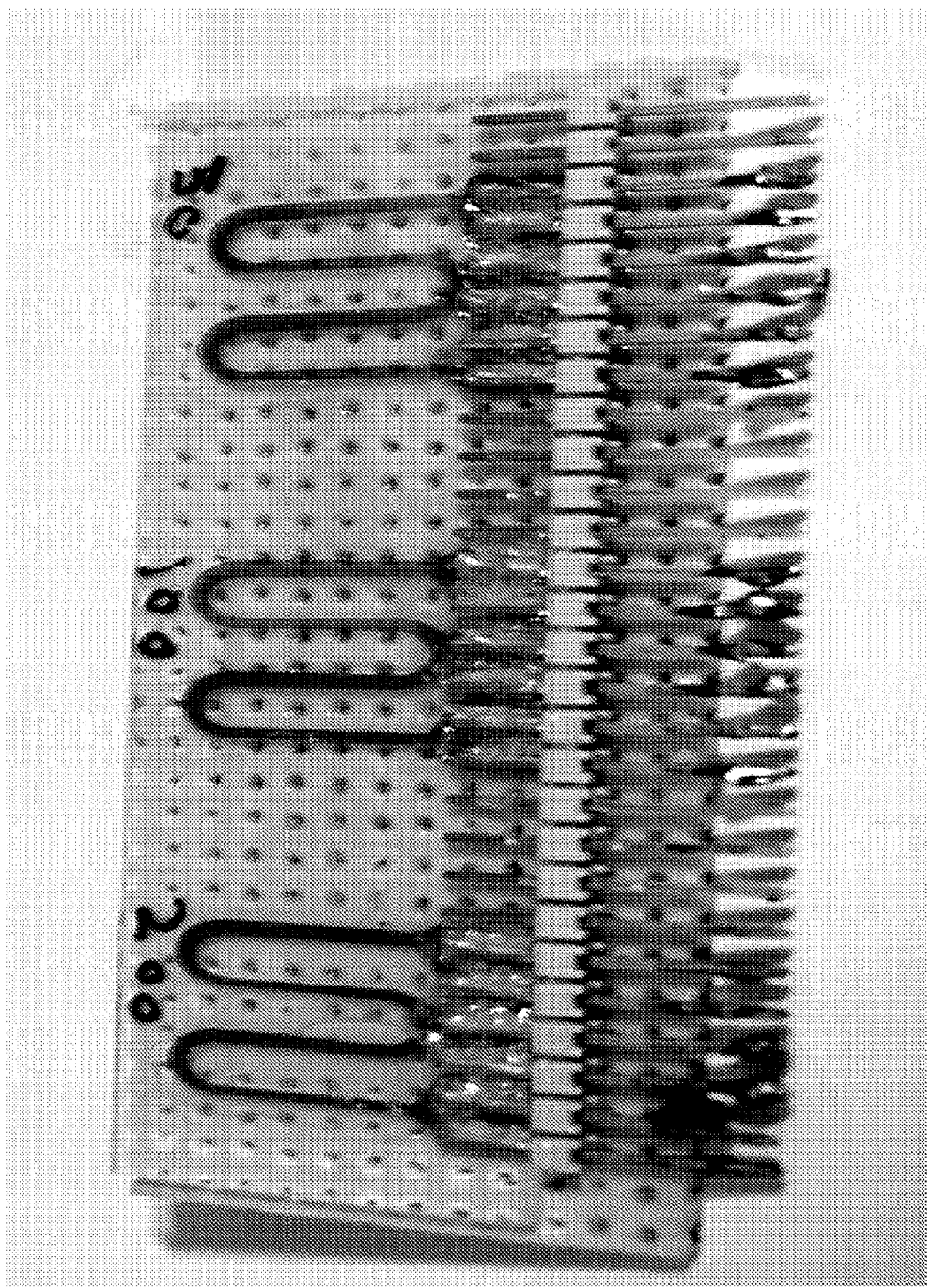
FIG. 3 is a photograph of a sample of a corrosion detection apparatus embodying the first exemplary apparatus of FIGS. 1E and 2 according to the first embodiment of the present disclosure.

Referring to FIG. 3, a photograph shows a sample of a corrosion detection apparatus embodying the first exemplary apparatus of FIGS. 1E and 2 is shown. In this sample, the sample of the first exemplary apparatus includes three corrosion sensors, each including a metal strip including a series connection of an exposed strip portion and a protected strip portion. The three metal strips have thicknesses of 50 nm, 100 nm, and 200 nm, respectively. The three metal strips were formed on a glass substrate by deposition of a metal film thereupon and lithographic patterning. For every corrosion sensor, the reference arm including the protected strip portion is protected by a transparent polymer film and the exposed arm in the exposed strip portion has been corroded. The metal films included silver and copper.

Figure 4:
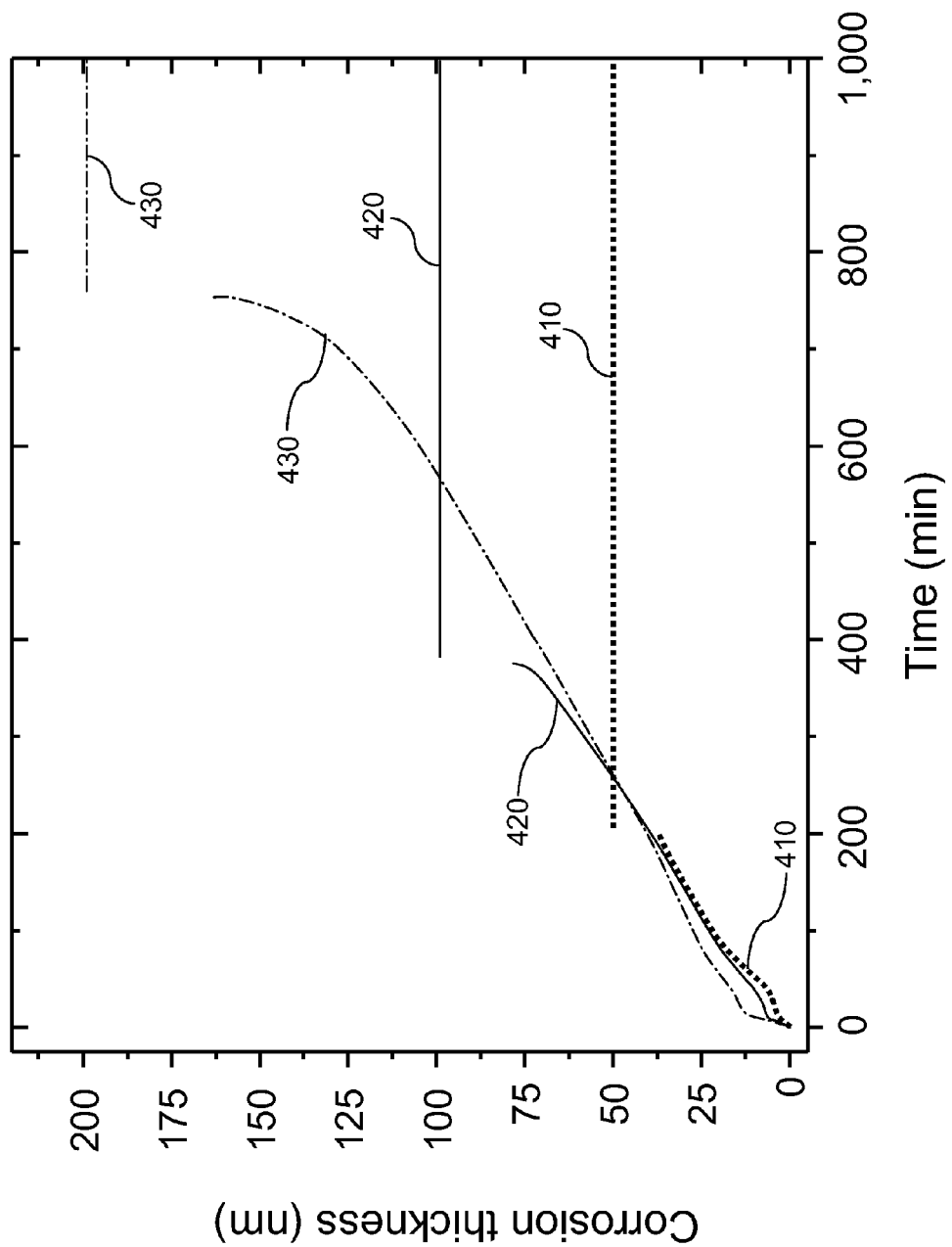
FIG. 4 is a graph showing measured corrosion data that was generated with a corrosion detection apparatus of the type shown in FIG. 2 according to the first embodiment of the present disclosure.

The sample of the corrosion detection apparatus shown in FIG. 3 was subjected to testing to provide corrosion data employing the circuitry shown in FIG. 2. Thus, all three corrosion sensors of the sample were connected to an electric detection circuit where the change in resistance for all three corroding resistors and all three reference resistors were simultaneously monitored while the corroding resistors were subjected to a corrosive environment. The measured corrosion data generated from the corrosion experiment above is plotted in FIG. 4. FIG. 4 includes three curves, i.e., a first curve 410, a second curve 420, and a third curve 420. The first curve 410 is based on measured resistance data from the first corrosion sensor including a 50 nm thick metal strip, the second curve 420 is based on measured resistance data from the second corrosion sensor including a 100 nm thick metal strip, and the third curve 430 is based on measured resistance data from the third corrosion sensor including a 200 nm thick metal strip. The 50 nm thick metal strip was completely corroded in about 200 minutes, the 100 nm thick metal strip was completely corroded in about 400 minutes, and the 200 nm thick metal strip was completely corroded in about 800 minutes. The apparent discontinuities that are present in the first, second, and third curves (410, 420, 430) at about 200 minutes, 400 minutes, and 800 minutes, respectively, are due to the onset of an electrical open in the corresponding metal strips as the film thickness is reduced below 1 nm and the conduction mechanism is changing.

The example illustrated in the graph of FIG. 4 demonstrates that the corrosion rate is the same for all three corrosion sensors employed in this case, and that the time required for complete corrosion for the 50 nm thick film, the 100 nm thick film, and the 200 nm thick film scales with the nominal thickness of the three metal films as expected. The first curve 410, the second curve 420, and the third curve 430 substantially overlap with one another. Particularly, the first curve 410 and the second curve overlap substantially between 0 min and 200 minutes, and the second curve 420 and the third curve overlap substantially between 200 minutes and 370 minutes. Further, the substantial overlap between the various curves (410, 420, 430) near the transition thicknesses, i.e., about 40 nm and 80 nm, makes it possible to switch from one corrosion sensor employing a metal strip having a lesser thickness to the a corrosion sensor employing a metal strip having a greater thickness at such transition thicknesses during the operation of the corrosion detection apparatus. For example, at 200 minutes into the measurement, data acquisition from the corrosion sensor employing the 100 nm thick metal strip can take over the data acquisition from the corrosion sensor employing the 50 nm thick metal strip. Similarly, at 400 minutes into the measurement, data acquisition from the corrosion sensor employing the 200 nm thick metal strip can take over the data acquisition from the corrosion sensor employing the 100 nm thick metal strip.

In general, when multiple functional corrosion sensors provide information on the corrosion rate at a location, the data from the functional corrosion sensor with the highest resolution in the corrosion rate can be selected because the accuracy of measurement increases with reduction in remaining uncorroded portion of the exposed portion of a metal strip. The functional corrosion sensor with the highest resolution in the corrosion rate is the thinnest functional metal strip in most instances. Employing different thickness films, the source of data acquisition in the corrosion detection apparatus can be switched from the thinnest conducting corroding resistor to another corroding resistor having the next least thickness. Thus, the corrosion detection apparatus can employ different corrosion sensors sequentially over an extended period of time while maintaining a high sensitivity level through the operation of the corrosion detection apparatus.

Further, the flexibility of manufacturing processing steps makes possible to deposit various metal films of different composition as well as of different thicknesses on the same substrate. Thus, the corrosive environment can be monitored employing, for example, both silver strips having different thicknesses and copper strips having different thicknesses located on the same substrate. In addition, the corrosion detection apparatus can be deployed both for monitoring indoor and outdoor environmental conditions in real time. By employing a plurality of metal strips having different thicknesses, ultrahigh corrosion rate sensitivity on the order of 3 nm per month can be provided, while at the same time, the lifetime of the corrosion detection apparatus can be greater than 1 year.

In general, a method detecting corrosion-accelerating gases can employ the corrosion detection apparatus as provided above. A first corrosion rate can be determined for a first time period at a location based on measured data on a resistance change in a first metal strip among the plurality of metal strips. Then, a second corrosion rate can be determined for a second time period at the location based on measured data on a resistance change in a second metal strip among the plurality of metal strips. The second metal strip is thicker than the first metal strip, and the second time period is a time period subsequent to the first time period. For any integer i greater than 1 and less than (n+1) in which n is the total number of metal strips in the plurality of metal strips, an i-th corrosion rate can be determined for an i-th time period at the location based on measured data on a resistance change in an i-th metal strip among the plurality of metal strips. The i-th metal strip is thicker than the (i−1)-th metal strip, and the i-th time period is a time period subsequent to the (i−1)-th time period. The beginning of the i-th time period may coincide with the end of the (i−1)-th time period.

Thus, the method of detecting corrosion-accelerating gases can optionally include sequentially determining whether at least one metal strip among the plurality of metal strips is electrically open in an order of increasing thickness among the plurality of metal strips beginning with a metal strip having a least thickness, and determining a corrosion rate at a location based on data from a first metal strip that is not electrically open during this sequential determination.

Optionally, the second time period can commence upon determination that the measured data on the resistance change in the first metal strip is not linear to an exposure time of the first metal strip. Likewise, for any integer i greater than 1 and less than (n+1), the i-th time period can commence upon determination that the measured data on the resistance change in the (i−1)-th metal strip is not linear to an exposure time of the (i−1)-th metal strip.

Referring to FIGS. 5A and 5B, a second exemplary apparatus for detection of corrosion-accelerating gases according to a second embodiment of the present disclosure can be formed employing the same processing steps as the processing steps of FIGS. 1A-1D, while modifying the patterns of the metal strips. Specifically, at least one metal film having multiple portions having different thicknesses are formed employing any method known in the art including the method illustrated in FIGS. 1A-1C. The multiple portions of the at least one metal film are patterned to form multiple metal strips, which can include a first metal strip 120, a second metal strip 130, a third metal strip 140, an (n−1)-th metal strip 150, and an n-th metal strip 160. The number n is any integer greater than 1, and for every integer greater than 1 and less than (n+1), the i-th metal strip is thicker than the (i−1)-th metal strip.

The relationship among the thicknesses of the n metal strips (120, 130, 140, 150, 160) can be identical to the relationship among the thicknesses of the n metal strips (20, 30, 40) in the first embodiment. Further, the absolute values of the thicknesses of the n metal strips (120, 130, 140, 150, 160) can be identical to the absolute values of the thicknesses of the n metal strips (20, 30, 40) in the first embodiment.

Multiple series of metal strips may be provided such that each series of metal strips includes a plurality of metal films including the same metal, while different series employs different metals for the metal strips. For example, one plurality of metal strips may include silver strips having different thicknesses, and another plurality of metal strips may include copper strips having different thicknesses.

Figure 6:
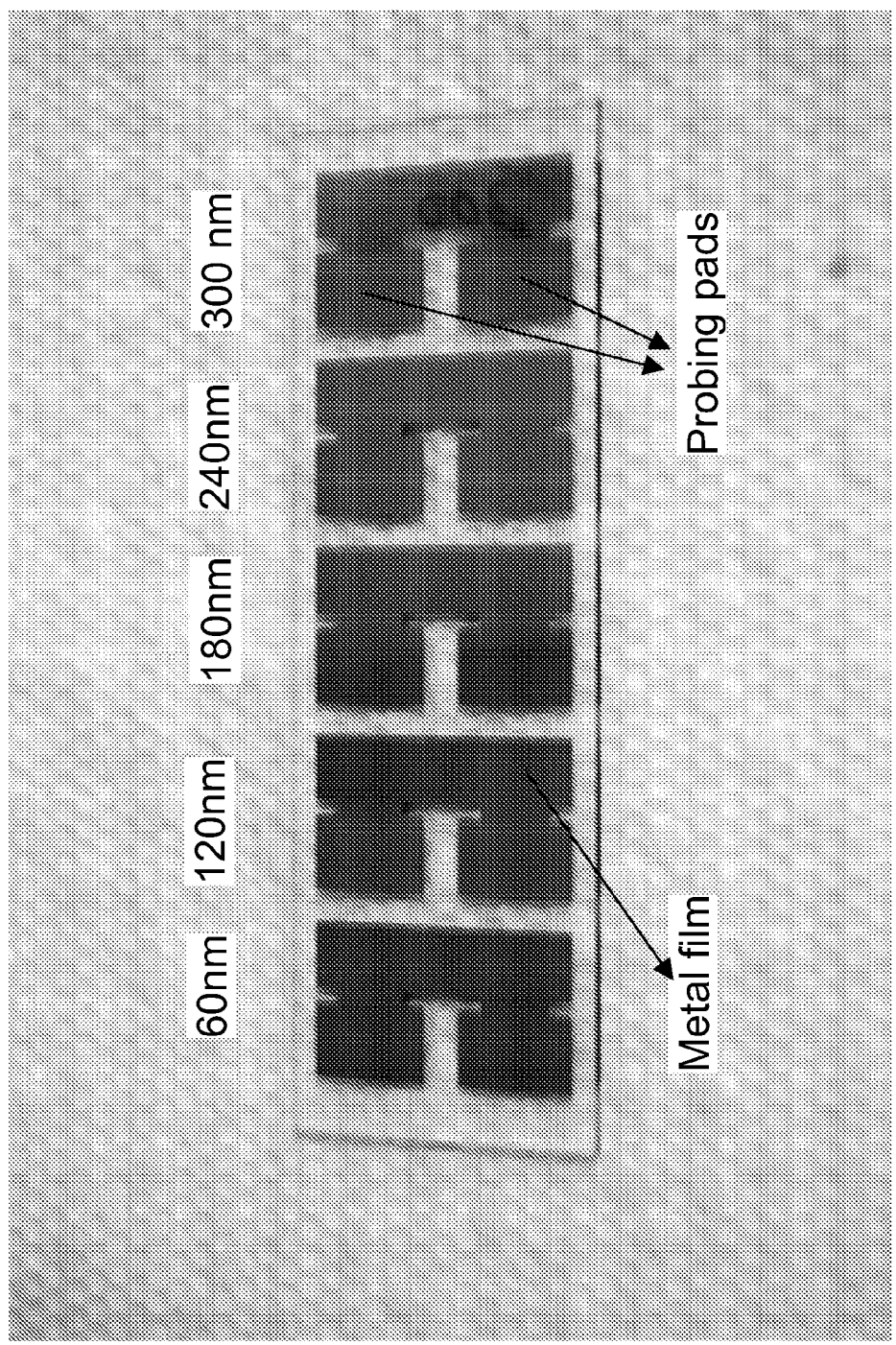
FIG. 6 is a photograph of a sample of the corrosion detection apparatus embodying the second exemplary apparatus of FIGS. 5A and 5B according to the second embodiment of the present disclosure.

Referring to FIG. 6, a photograph shows a sample of the corrosion detection apparatus embodying the second exemplary apparatus of FIGS. 5A and 5B according to the second embodiment of the present disclosure. The sample of the corrosion detection apparatus includes five metal strips having thicknesses of 60 nm, 120 nm, 180 nm, 240 nm, and 300 nm, respectively.

This type of corrosion detector apparatus does not employ differential comparison between the resistance of a corroding resistor and a reference resistor, but relies on individual probing of resistance on each corrosion sensor at a certain moment of time. Specifically, corrosion detection apparatus is exposed to a corrosive environment. As the corrosion process proceeds, each metal film is gradually corroded such that thinner metal films are consumed earlier than thicker metal films. The film resistance is probed manually by accessing the two end pads with a voltmeter to determine if each metal film is conductive or non-conductive.

As in the first embodiment, it can be sequentially determined whether at least one metal strip among the plurality of metal strips is electrically open in an order of increasing thickness among the plurality of metal strips beginning with a metal strip having a least thickness. Once the first conducting metal film is identified, the corrosion rate at the location can be determined based on data from the first metal strip that is not electrically open during this sequential determination.

At a transition from a completely corroded film, i.e., a nonconductive film, to a conductive film, the corrosion rate can be determined to be within a certain range, i.e., between a lower estimate and an upper estimate. Techniques for providing estimation as illustrated in FIG. 4 can be employed. Further, a rough estimate of corrosion rate can also be provided based on estimation of an upper bound and a lower bound of corrosion thickness. In this case, the estimate of the corrosion rate can be obtained by dividing the upper bound and the lower bound by the total time period that the corrosion detection sensor has been exposed to the corrosive ambient.

The manual probing method may be desirable at locations where real-time monitoring due to lack of power access. The changes in resistance measured either through real-time monitoring or manual monitoring can be assessed by extracting the thickness of the film from a look up table that relate the measured resistance of the corroding resistor, i.e., the exposed portion of the metal strip, to the film thickness. An illustrative exemplary look up table that provides such information of a metal film having an initial thickness of 120 nm and an initial resistance of 8.0 Ohms is provided below.

TABLE 1

An illustrative exemplary look up table for conversion of measured resistance to the thickness of uncorroded portion of a metal film having an initial thickness of 120 nm and an initial resistance of 8.0 Ohms.

| Resistance (Ohms) | Thickness of conductive portion (nm) |
|---|---|
| 8 | 120.0 |
| 9 | 106.7 |
| 10 | 96.0 |
| 11 | 87.3 |
| 12 | 80.0 |
| 13 | 73.8 |
| 14 | 68.6 |
| 15 | 64.0 |
| 20 | 48.0 |
| 25 | 38.4 |
| 30 | 32.0 |
| 35 | 27.4 |
| 40 | 24.0 |
| 45 | 21.3 |
| 50 | 19.2 |
| 55 | 17.5 |
| 60 | 16.0 |
| 65 | 14.8 |
| 70 | 13.7 |
| 75 | 12.8 |
| 80 | 12.0 |
| 90 | 10.7 |
| 100 | 9.6 |
| 110 | 8.7 |
| 120 | 8.0 |
| 130 | 7.4 |
| 140 | 6.9 |
| 150 | 6.4 |
| 160 | 6.0 |
| 170 | 5.6 |
| 180 | 5.3 |
| 190 | 5.1 |
| 200 | 4.8 |
| 210 | 4.6 |
| 220 | 4.4 |
| 230 | 4.2 |
| 240 | 4.0 |
| 250 | 3.8 |

TABLE 1-continued

An illustrative exemplary look up table for conversion of measured resistance to the thickness of uncorroded portion of a metal film having an initial thickness of 120 nm and an initial resistance of 8.0 Ohms.

| Resistance (Ohms) | Thickness of conductive portion (nm) |
|---|---|
| 300 | 3.2 |
| 400 | 2.4 |
| 500 | 1.9 |
| 600 | 1.6 |

While the present disclosure has been particularly shown and described with respect to preferred embodiments thereof, it will be understood by those skilled in the art that the foregoing and other changes in forms and details can be made without departing from the spirit and scope of the present disclosure. It is therefore intended that the present disclosure not be limited to the exact forms and details described and illustrated, but fall within the scope of the appended claims.

What is claimed is:

1. A corrosion detection apparatus comprising:
a plurality of metal strips located on an insulating surface of a substrate, wherein each of the plurality of metal strips has a different thickness in a direction substantially perpendicular to the insulating surface of the substrate than another of the plurality of metal strips,
wherein each of the plurality of metal strips is comprised of:
an exposed strip portion that is permeable to a corrosion-accelerating gas; and
a protected strip portion that is not permeable to the corrosion-accelerating gas,
wherein the exposed strip portion and the protected strip portion of the each of the plurality of metal strips are connected in a series connection.

2. The corrosion detection apparatus of claim 1, wherein the different thicknesses of the plurality of metal strips are integer multiples of a minimum thickness among the different thicknesses.

3. The corrosion detection apparatus of claim 1, wherein differences in thicknesses of the plurality of metal strips are integer multiples of a difference between a pair of metal strips among the plurality of metal strips.

4. The corrosion detection apparatus of claim 3, wherein the difference between the pair of metal strips is in a range from 3 nm to 250 nm.

5. The corrosion detection apparatus of claim 1, wherein the different thicknesses of the plurality of metal strips are in a range from 3 nm to 1,000 nm.

6. The corrosion detection apparatus of claim 5, wherein the different thicknesses of the plurality of metal strips are in a range from 25 nm to 500 nm.

7. The corrosion detection apparatus of claim 1, wherein each metal strip among the plurality of metal strips has a substantially constant width in a direction substantially parallel to the insulating surface.

8. The corrosion detection apparatus of claim 1, wherein each metal strip among the plurality of metal strips is comprised of a metal that is susceptible to corrosion by at least one of $H_2S$, $SO_2$, $NO$, $NO_2$, $N_2O_3$, $Cl_2$, and $O_3$.

9. The corrosion detection apparatus of claim 8, wherein each metal strip among the plurality of metal strips is comprised of a metal selected from silver, copper, brass, aluminum, zinc, and iron.

10. The corrosion detection apparatus of claim 1, wherein within each metal strip, the exposed strip portion and the protected strip portion have a same resistance.

11. The corrosion detection apparatus of claim 1, wherein within each metal strip, the exposed strip portion and the protected strip portion have a same width in a direction substantially parallel to the insulating surface, wherein the same width is greater than ten times the thickness of the each metal strip.

12. The corrosion detection apparatus of claim 1, wherein within each metal strip, the exposed strip portion and the protected strip portion have a same length in a direction substantially parallel to the insulating surface, wherein the same length is greater than one hundred times the thickness of the each metal strip.

13. The corrosion detection apparatus of claim 1, further comprising:
   a current source configured to provide electrical current through the exposed strip portion and the protected strip portion within a metal strip of the plurality of metal strips;
   a first voltmeter configured to measure a voltage difference across the exposed strip portion; and
   a second voltmeter configured to measure a voltage difference across the protected strip portion.

14. The corrosion detection apparatus of claim 1, wherein the protected strip portion is covered by a dielectric material that is not permeable to the corrosion-accelerating gas.

15. A method of forming a corrosion detection apparatus, the method comprising:
   forming a plurality of metal strips on an insulating surface of a substrate, wherein each of the plurality of metal strips has a different thickness in a direction substantially perpendicular to the insulating surface of the substrate than another of the plurality of metal strips; and
   forming, in each of the plurality of metal strips:
      an exposed strip portion that is permeable to a corrosion-accelerating gas, and
      a protected strip portion that is not permeable to the corrosion-accelerating gas,
      wherein the exposed strip portion and the protected strip portion of the each of the plurality of metal strips are connected in a series connection.

16. The method of claim 15, further comprising:
   forming a first contact pad on one end of each metal strip among the plurality of metal strips and a second contact pad on another end of the each metal strip among the plurality of metal strips.

17. The method of claim 15, wherein the exposed strip portion and the protected strip portion are formed in each of the plurality of metal strips by:
   depositing a dielectric material that is not permeable to the corrosion-accelerating gas over the plurality of metal strips; and
   patterning the dielectric material to form the exposed strip portion and the protected strip portion, wherein the exposed strip portion is exposed to the corrosion-accelerating gas, and the protected strip portion is covered by the dielectric material.

18. The method of claim 15, wherein in forming the plurality of metal strips on the insulating surface of the substrate, the different thicknesses of the plurality of metal strips are integer multiples of a minimum thickness among the different thicknesses.

* * * * *